United States Patent [19]

Takahashi et al.

[11] 4,453,808
[45] Jun. 12, 1984

[54] APPARATUS FOR DETECTING THE POSITION OF A PATIENT'S EYE IN OPHTHALMOLOGIC INSTRUMENTS

[75] Inventors: Susumu Takahashi; Yasuo Kato; Yoshinori Oana; Yoshiyuki Hatano, all of Tokyo, Japan

[73] Assignee: Tokyo Kogaku Kikai Kabushiki Kaisha, Japan

[21] Appl. No.: 390,978

[22] Filed: Jun. 22, 1982

[30] Foreign Application Priority Data

Jun. 25, 1981 [JP] Japan ................................. 56-98927
Jun. 25, 1981 [JP] Japan ................................. 56-98928

[51] Int. Cl.³ ............................................. A61B 3/14
[52] U.S. Cl. ..................................................... 351/208
[58] Field of Search ....................... 351/206, 207, 208; 354/62

[56] References Cited

U.S. PATENT DOCUMENTS 4,253,743  3/1981  Matsumura ..................... 354/62 X

*Primary Examiner*—John K. Corbin
*Assistant Examiner*—Rodney B. Bovernick
*Attorney, Agent, or Firm*—Brumbaugh, Graves, Donohue & Raymond

[57] ABSTRACT

In an ophthalmoscopic instrument such as an eye fundus camera or an eye refractometer, a device is provided for detecting the position of a patient's eye. The device includes a target projecting system for projecting a light beam to the patient's eye, an imaging lens for imaging the light beam as reflected at the patient's eye and a detector for sensing the reflected light beam. A chopper is provided for selectively passing the reflected light beam to the detector for making it possible to produce a signal which includes informations of imaging condition of the light beam at the detector.

5 Claims, 12 Drawing Figures

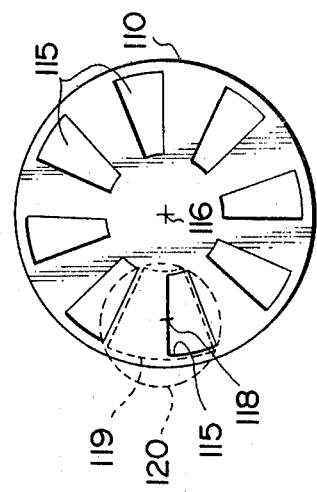
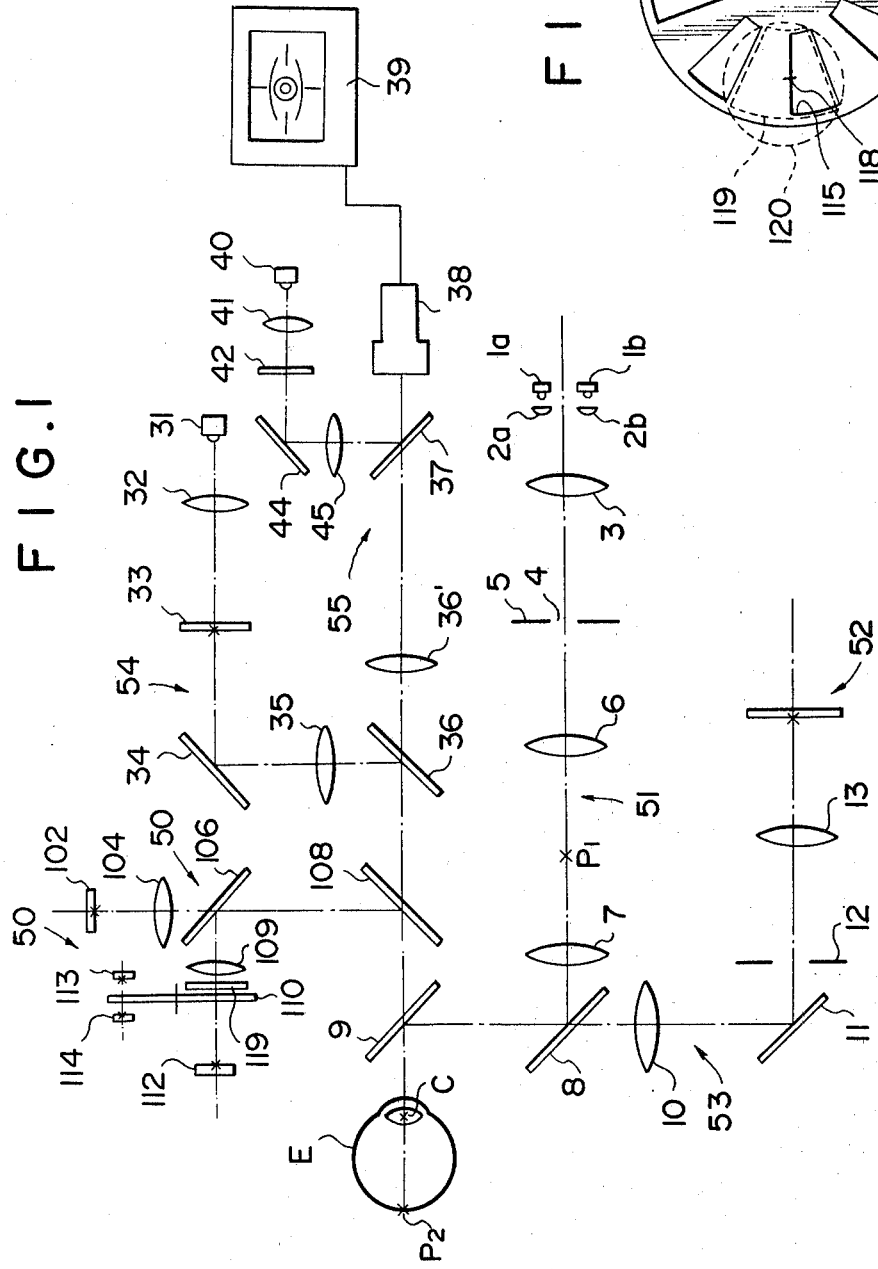

FIG.3
(A) 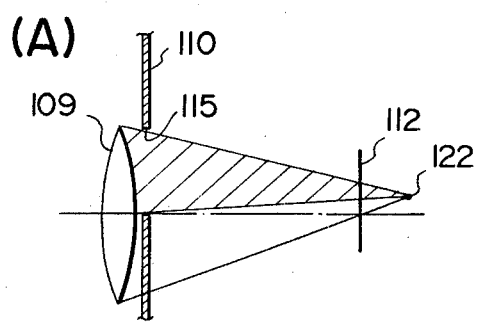
(B) 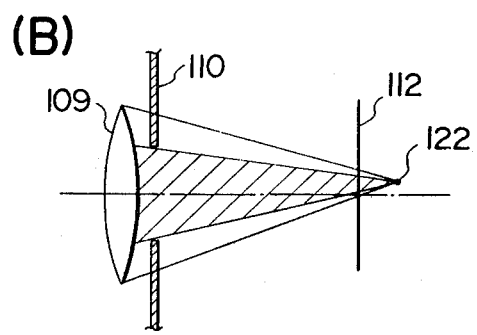
(C) 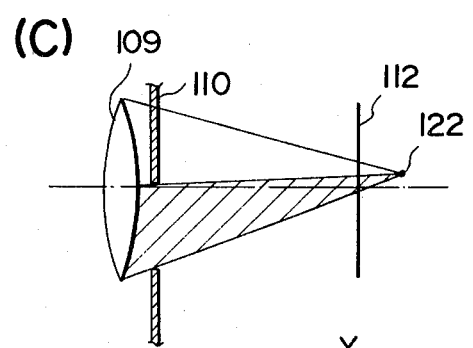
FIG.4
(A) 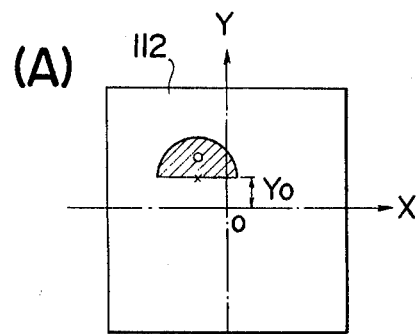
(B) 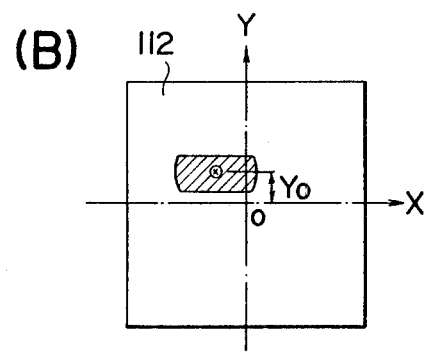
(C) 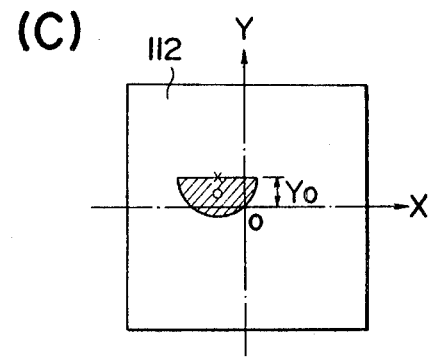

FIG.6
(A)
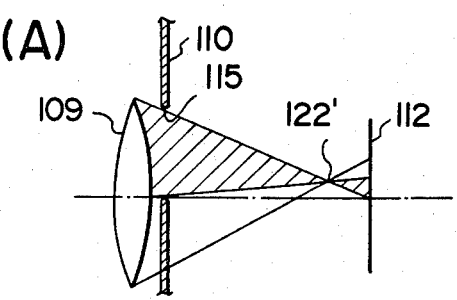
(B)
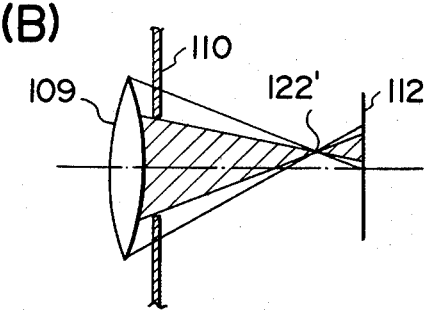
(C)
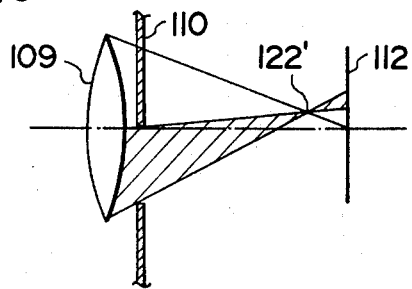
FIG.7
(A)
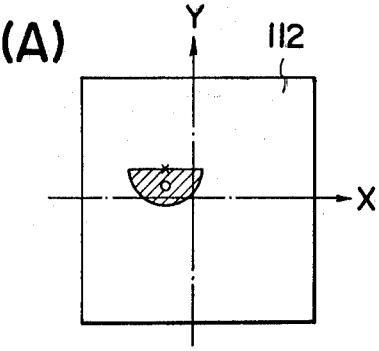
(B)
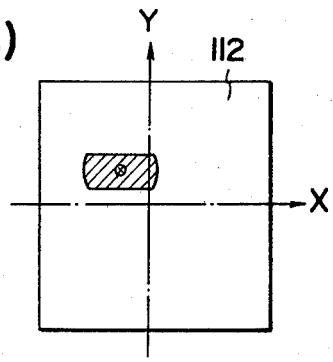
(C)
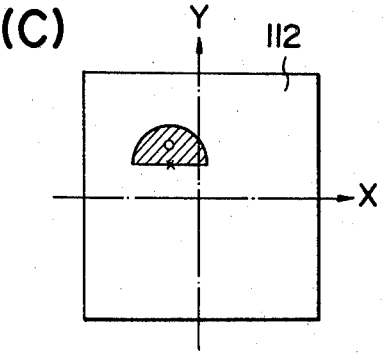
FIG.8
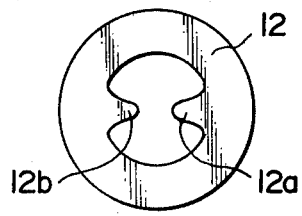
FIG.9
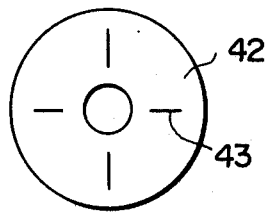

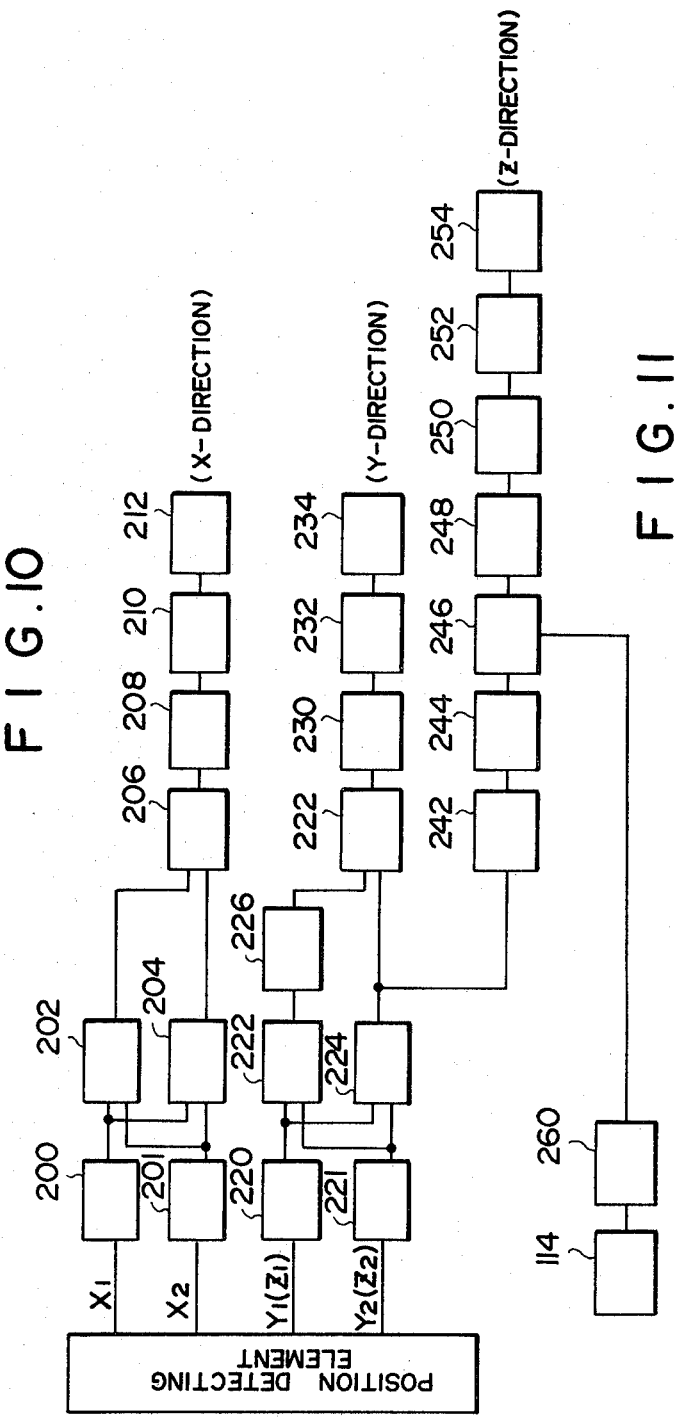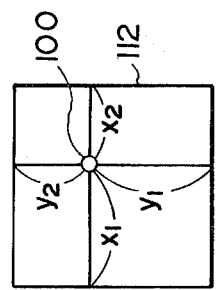

FIG. 12
(A) 
(B) 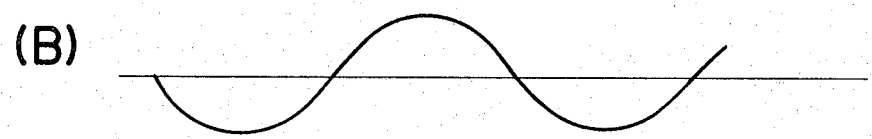
(C) 
(D) 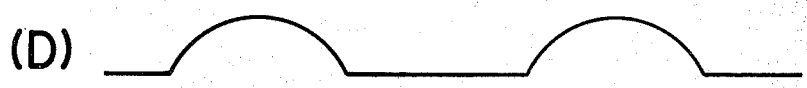
(E) 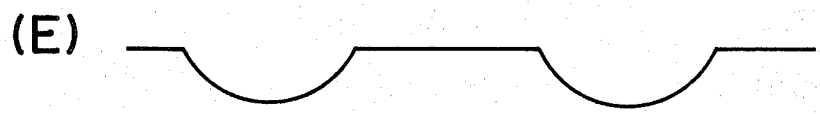
(F) 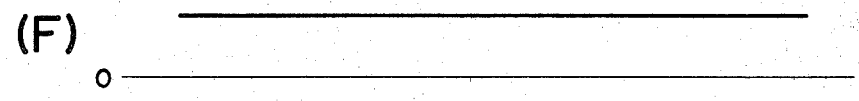
(G) 

APPARATUS FOR DETECTING THE POSITION OF A PATIENT'S EYE IN OPHTHALMOLOGIC INSTRUMENTS

The present invention relates to an apparatus for detecting the relative position between an ophthalmologic instrument and an eye to be examined.

In such an ophthalmologic instrument such as eye refractometers, funduscopic cameras or the like, it is required that the instrument is properly positioned relative to an eye to be examined prior to start of operation. In order to fulfill such a requirement, there have been proposed many kinds of systems for detecting the position of an eye to be examined relative to an examination instrument. For example, there have been proposed relatively simple systems which are adapted only to detect deviation of a patient's eye from its proper position but cannot detect the direction of deviation. It is therefore difficult to adjust the instrument into its proper position. There have also been known such systems that can detect both the amount and direction of deviation of a patient's eye from its proper position but such systems are disadvantageous because they require complicated mechanisms.

It is therefore an object of the present invention to provide a simple apparatus for detecting the position of an eye to be examined in ophthalmologic instruments which can easily measure and detect the amount and direction of deviation of an eye to be examined from its proper position, particularly along the optical axis of an ophthalmological instrument used.

Another object of the present invention is to provide an apparatus for photoelectrically detecting the position of a light source or secondary light source at higher speed with more precision, which can be used in the above apparatus according to the present invention.

In one aspect of the present invention, the apparatus for detecting the position of an eye to be examined in an ophthalmologic instrument comprises a light source for projecting along an optical axis a beam of light toward an eye to be examined, lens means for imaging the light beam reflected at a front portion of said eye to be examined, means for causing the light beam from said imaging lens means to scan at least in one direction, and means for detecting the position of said light source by sensing the position of said light beam transmitted through said scanning means, said light source detecting means being adapted to provide a signal which can be used to detect relative position between said eye to be examined and said ophthalmologic instrument at least along the optical axis thereof.

In another aspect of the present invention, the light source detecting means includes a photoelectric system for detecting the position of said light source in a linear direction between said light source and said light source detecting means.

The above or other objects and features will be apparent from the following detailed descriptions of a preferred embodiment taking reference to the accompanying drawings, in which;

FIG. 1 is a schematic view of the optical system of an eyefundus camera in accordance with one embodiment of the present invention;

FIG. 2 is a front elevational view of a chopper which is used in the embodiment shown in FIG. 1;

FIGS. 3 through 7 illustrate the principle of detection used in the present invention;

FIG. 8 is a front elevational view of an aperture for blocking the reflected light;

FIG. 9 is a front elevational view of a collimation scale;

FIG. 10 is a block diagram of an electric circuit used in the embodiment shown in FIG. 1;

FIG. 11 illustrates the output signal of a secondary light receiving element; and, FIG. 12 shows various waveforms in the electric circuit shown in FIG. 10.

Figure 5:
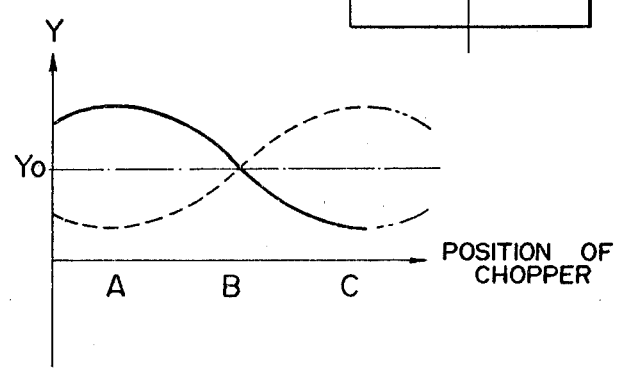

Referring to FIG. 1, an embodiment of the present invention is shown to be applied to an auto-refractometer which comprises a system 50 for detecting the position of an eye to be examined, an optical system 51 for projecting a measurement target onto the fundus of the eye to be examined, a two-dimensional detector 52 for detecting the amount of deviation in the image of said measurement target, an optical system 53 for receiving and projecting the measurement target image formed on the eye fundus onto the two-dimensional detector 52, a viewing target projecting system 54 for fixing the viewing axis of the eye to be examined, and an optical sighting system 55 for displaying the positional relation between the eye to be examined and the auto-refractometer.

The system 50 for detecting the position of the eye to be examined comprises a light emitting element 102, a projector lens 104, a first half mirror 106 and a second half mirror 108 having an optical reflection axis on which the above other components are disposed. On the optical reflection axis of the first half mirror 106 are disposed an imaging lens 109, a chopper 110 and a two-dimensional light receiving element 112. The system 50 further comprises a light emitting element 113 providing a reference signal which is disposed adjacent to the chopper 110 at one side and a light receiving element 114 receiving the reference signal which is located adjacent to the chopper 110 at the other side thereof. The light emitting and receiving elements 102 and 112 are positioned at locations which are conjugate with the middle point C between the apex and the center of curvature in the cornea of the eye to be examined (focal point if the cornea is assumed to be a convex mirror), the projector lens 104 and the imaging lens 109. In other words, if the eye to be examined E is properly positioned, the beam of light reflected at the cornea of the eye E becomes a pencil of parallel rays, so that the image of the light emitting element 102 will be formed on the light receiving element 112. As shown in FIG. 2, the chopper 110 includes a disc having a plurality of sector slits 115 and being rotatable about its center 116. An optical axis 118 passes substantially through a point on the outer periphery of a circle including the centers of the sector slits 115. An aperture 119 is disposed between the chopper 110 and the imaging lens 109 and adapted to maintain the quantity of light incident on the light receiving element 112 constant. This aperture 119 has an opening two times that of each of the sector slits 115. At the sector slits 115, the light beam 120 corresponds substantially to a circumcircle in the opening of the aperture 119.

The principle of detection in the eye-position detecting system 50 aforementioned will now be described. If a point of image 122 formed by the imaging lens 109 is rearwardly of the light receiving element 112 or at the side opposite to the imaging lens 109, a certain sector slit 115 is passed as the chopper 110 is rotated across the light beam from the imaging lens 109 through steps as shown at A, B and C in FIG. 3. Therefore, such light beams sequentially form images as shown at A, B and C in FIG. 4 on the light receiving element 112. In FIG. 4, the symbol $X$ designates a position through which the optical axis passes while the symbol $O$ denotes the center of the cross-section of the incident light beam. At this time, the light receiving element 112 generates a detection signal as shown by solid line in FIG. 5 in which the horizontal axis represents the position of the chopper and the vertical axis indicates coordinates in Y-axis direction.

If a point of image 122' formed by the imaging lens 109 is in a position forwardly of the light receiving element 112 or at the same side of the imaging lens 109, the light beam incident on the light receiving element 112 form images as the chopper 110 is rotated sequentially as shown in FIG. 7. FIGS. 6 and 7 correspond to FIGS. 3 and 4, respectively. The light receiving element 112 generates a detection signal as shown by a broken line in FIG. 5.

If a point of image from the imaging lens 109 coincides with the surface of the light receiving element 112, the latter generates a detection signal in the form of a linear line parallel to the horizontal axis as shown by chain line in FIG. 5.

Thus, it will be understood that the detection signal from the light receiving element 112 indicates the location of the image point relative to the light receiving element 112. In other words, detection can be made on the direction and amount of deviation of the cornea apex in the eye from a predetermined location along the optical axis. At the same time, by detecting coordinates of a mean incident location on the light receiving element 112, it can be detected how much the position of cornea apex in the eye to be examined deviates from a proper position in all the directions. Although the illustrated embodiment has been described with respect to such an arrangement in that the light receiving element 112 is disposed at a position conjugate with the middle point C between the apex and center of curvature in the cornea of the eye to be examined E when the eye is in its proper position, the light receiving element 112 may be located at a position conjugate with the apex or center of curvature in the cornea of the eye to be examined E.

The optical system for projecting the target 51 as shown in FIG. 1, comprises a pair of infrared sources $1a$ and $1b$ disposed symmetrically about the optical axis, condenser lenses $2a$ and $2b$ respectively condensing the light beams from the infrared sources $1a$ and $1b$, a collimator lens 3, a measurement target 5 having an aperture 4 of circular opening, an imaging lens 6, an imaging lens 7 for projection, a half mirror 8 for infrared rays, and a dichroic mirror 9 having such characteristics that it reflects infrared rays of longer wavelength and transmits infrared rays at and adjacent the visible range. The above pair of infrared sources $1a$ and $1b$ are alternately lighted on at a high speed and revolve about the optical axis as a unit.

The rays from the pair of infrared sources $1a$ and $1b$ are condensed respectively by the condenser lenses $2a$ and $2b$ and further collimated by the collimator lens 3 before they are obliquely incident on the circular aperture 4. After passing through the circular aperture 4, the light beam is imaged at a point $P_1$ by the imaging lens 6 and then incident on the eye to be examined E through the imaging lens 7, half mirror 8 and dichroic mirror 9. Thus, the images of the infrared sources $1a$ and $1b$ are formed at the pupil of the eye to be examined E while the image of the circular aperture 4 in the measurement target 5 is formed at the fundus $P_2$ of the eye to be examined. If the measurement target 5 is conjugate with the fundus $P_2$ of the eye to be examined E, the image of the circular aperture 4 illuminated by the light from the infrared source $1a$ is formed on the fundus $P_2$ at the same position as that of the image of the circular aperture 4 illuminated by the light from the infrared source $1b$. On the other hand, if the measurement target 5 is not conjugate with the fundus $P_2$ of the eye to be examined E, the images of the circular aperture 4 illuminated by the respective infrared sources are separately formed on the fundus $P_2$ at two locations thereof.

The optical system 53 for receiving the light from the target, as shown in FIG. 1, comprises the dichroic mirror 9, the half mirror 8, an objective lens 10 for receiving the light, a mirror 11, an aperture 12 disposed at a position conjugate with the cornea of the eye to be examined relative to the objective lens 10 and adapted to block the light reflected at the cornea, and a relay lens 13. The aperture 12 is, as shown in FIG. 8, in the form of a plate having a substantially circular opening and two light blocking portions $12a$ and $12b$ which are formed therein to inwardly extend from the periphery of the opening symmetrically with respect to a position through which the optical axis passes. Further, the aperture 12 is adapted to rotate with the infrared sources $1a$ and $1b$ which are rotated about the optical axis. Still further, the aperture 12 is disposed at the forward focal point of the relay lens 13. Therefore, the optical projection system including the relay lens 13 becomes resemblant to a telecentric system.

In such an arrangement, the measurement target image on the fundus $P_2$ of the eye to be examined is projected onto the two-dimensional detector 52 through the dichroic mirror 9, half mirror 8, objective lens 10, mirror 11 and relay lens 13. At this time, any harmful light reflected from the cornea of the eye to be examined is eliminated by the light blocking protrusions $12a$ and $12b$ in the aperture 12. Since the aperture 12 and relay lens 13 define an optical system resemblant to a telecentric system, the measurement target image formed on an optical metering system 14 will be made of a light beam including a principal ray parallel to the optical axis and have such a characteristics that the center of the measurement target image in the form of a circular opening will not be offset even at a position forwardly or rearwardly of the image position.

The two-dimensional detector 52 is adapted to discriminate whether the images of the circular aperture 4 on the eye fundus are aligned with or separated from each other under the alternate energization of the infrared sources $1a$ and $1b$ and then to measure a distance between the separated images. The resulting measurement is used in a known operational circuit to calculate the refracting power of the eye to be examined in the meridian direction along which the infrared sources $1a$ and $1b$ are arranged.

The viewing target projecting system 54 comprises, as shown in FIG. 1, a source of visible light 31, a condenser lens 32, a viewing target 33 movable along the optical axis, a mirror 34, a projector lens 35, and a dichroic mirror 36 adapted to reflect the visible light, but to transmit the infrared light.

In such an arrangement, the light from the source of visible light 31 illuminates the target 33 through the condenser lens 32. The light from the target 33 is projected onto the eye to be examined E through the mirror 34, the projector lens 35, the dichroic mirror 36 and the half mirror 9. The eye to be examined is thus fixed along the viewing axis by letting the patient watch the viewing target 33. It is required that the eye to be examined is always in a far sighting state so that the target 33 is adjusted to such a far sighting position.

The optical sighting system 55 comprises the half mirror 9, the dichroic mirror 36, a projector lens 36', a half mirror 37 and an image pickup tube 38 all of which are disposed on the same optical axis. The system 55 also comprises a source of light 40, a condenser lens 41, a collimation plate 42, a mirror 44 and a projector lens 45 all of which are disposed on the optical reflection axis of the half mirror 37. The image pickup tube 38 is connected with a monitoring TV set 39. As shown in FIG. 9, the collimation plate 42 has a collimation scale 43 including a central circle and radial lines extending from the central circle.

In the optical sighting system thus constructed, onto the image pickup tube 38 are projected two overlapped images, one image being that of the front part of the eye E from the projector lens 36' and the other image being that of the collimation scale 43 from a projector lens 45. Observing the monitoring TV 39, the operator moves and adjusts the ophthalmologic instrument relative to the eye to be examined such that the center of the pupil image be aligned with the image of the collimation scale 43 while at the same time the optical axis of the eye correspond to the optical axis of the optical system 52 for receiving the target image.

In the above arrangement and operation, the refracting powers of the eye to be examined are measured in at least three meridian directions with the resulting measurements being used to obtain the diopter and the degree and direction of astigmatism in the eye to be examined.

With reference to FIG. 10, there will now be described an electric circuitry for moving the body of the auto-refractometer on the basis of signals detected by the two-dimensional light receiving element 112 of the eye-position detecting system 50 to provide a proper relative position between the eye to be examined and the suto-refractometer. If a beam of light 100 is incident on the light receiving element 112 as shown in FIG. 11, the latter generates output voltages $X_1$, $X_2$, $Y_1$ and $Y_2$ corresponding to distances $x_1$, $x_2$, $y_1$ and $y_2$ which relate to the incident position in the coordinate system. If the light beam 100 is incident on the center of the light receiving element 112, $X_1$ and $Y_1$ are equal to $X_2$ and $Y_2$, respectively. This embodiment is now assumed that the light beam is scanned by the rotation of the chopper 110 in Y-direction.

First of all, descriptions will be made on a circuitry for detecting and adjusting a deviation in the horizontal direction, that is, X-direction. The terminals of outputs $X_1$, $X_2$ in the light receiving element 112 are respectively coupled with the inputs of amplifying circuits 200 and 201 which are in turn connected to a subtraction circuit 202 for obtaining a subtraction $(X_1-X_2)$ and an adding circuit 204 for performing a culculation based on the equation $(X_1+X_2)$, respectively. These subtraction and adding circuits 202 and 204 are coupled with a division circuit 206 for performing calculation based on the equation $(X_1-X_2)/(X_1+X_2)$ which is in turn connected with a motor 212 through a direction discriminating circuit 208 for judging plus or minus in the quotient of $(X_1-X_2)/(X_1+X_2)$, and a driver 210. In such a circuitry, since the scan is made by the chopper 110 in Y-direction, the signals $X_1$ and $X_2$ indicative of a mean location of the light beam 100 are produced at a constant level independently of the amount of deviation on the eye to be examined unless the quantity of light incident on the light receiving 112 is changed. The output signals $X_1$ and $X_2$ from the light receiving element 112 are respectively amplified by the amplifying circuits 200 and 201, and then the respective operation $(X_1-X_2)$ and $(X_1+X_2)$ are made in the subtraction and addition circuits 202 and 204, respectively. The outputs of the subtraction and addition circuits 202, 204 are calculated by the division circuit 206 as aforementioned. This enables the electric circuitry to obtain an electric signal at an invariable level corresponding to the coordinate position of an incident beam of light. The absolute value of $(X_1-X_2)/(X_1+X_2)=X$ indicates the amount of deviation on the eye to be examined in X-direction. The output of the division circuit 206 is coupled with the input of the direction discriminating circuit 208 wherein the above value is judged on plus or minus. The plus or minus symbol of the value X indicates one of the opposite orientations on a deviation in X-direction. Thus, the driver 210 drives the motor 212 in either of the opposite directions to adjust the deviation in X-direction.

A circuitry for detecting and adjusting a deviation in the vertical direction, that is, Y-direction will now be described. Because the scanning is made by the chopper 110 in Y-direction as described hereinbefore, voltage signals $Y_1$ and $Y_2$ outputted from the light receiving element 112 will be modulated signals corresponding to this scanning. As described with the principle of the eye-position detecting system 50 hereinbefore, the voltage signals $Y_1$ and $Y_2$ contain information in Z-direction, that is, in the longitudinal direction of the auto-refractometer. Therefore, these voltage signals will be designated by $Y_1(Z_1)$ and $Y_2(Z_2)$. The terminals of the outputs $Y_1(Z_1)$ and $Y_2(Z_2)$ from the light receiving element 112 are respectively coupled with substraction and addition circuits 222 and 224 through the respective amplifying circuits 220 and 221. The subtraction circuit 222 is coupled with a division circuit 228 through a lowpass filter 226 while the addition circuit 224 is connected directly with the same division circuit 228. This division circuit 228 is connected with a motor 234 through a direction discriminating circuit 230 and driver 232 as in the aforementioned X-direction circuitry. The operation of this circuitry is identical with that of the said X-direction circuitry except that the low-pass filter 226 eliminates any modulated component in the output signal from the subtraction circuit 222, that is, any influence of the signals $Z_1$ and $Z_2$ to provide a voltage at constant level. Similarly, plus or minus in $(Y_1-Y_2)/(Y_1+Y_2)$ is discriminated such that the driver 232 drives the motor 234 to adjust a deviation in Y-direction.

An electric circuitry for detecting and adjusting a deviation in Z-direction will finally be described. In the Z-direction circuitry, the subtraction and addition circuits 222, 224 in the above Y-direction circuitry are coupled directly with a division circuit 242 which is connected with a motor 254 through a band pass filter 244, a synchronous commutator circuit 246, a low-pass filter 248, a direction discriminating circuit 250 and a driver 252. The reference signal detecting element 114 is coupled with the synchronous commutator circuit 246 through an amplifying circuit 260. In this circuitry, the division circuit 242 calculates a signal $Y_1(Z_1$-

)$-Y_2(Z_2)/Y_1(Z_1)+Y_2(Z_2)$ with the calculated result being inputted to the band-pass filter 244 the output of which generates a modulated wave having an amplitude proportional to the amount of deviation in Z-direction. This modulated wave is varied in phase depending on the direction of deviation as shown by A, B in FIG. 12. On the other hand, the output of the reference signal detecting element 114 is amplified by the amplifying circuit 260 to provide a reference signal in the form of a square wave as shown by C in FIG. 12. This reference signal is coupled with the synchronous commutator circuit 246 wherein this reference signal and the output of the band pass filter 244 are synchronously commutated to provide an output signal in the form of a wave which can be varied depending on the direction of deviation as shown by D or E in FIG. 12. The output of the synchronous commutator circuit 246 is converted by the low-pass filter 248 into a signal as shown by F or G in FIG. 12 and then inputted to the direction discriminating circuit 250 wherein this signal is judged on plus or minus. The plus or minus signal indicates the direction of deviation and is inputted to the driver 254 to drive the motor 254.

Although the invention has been described with respect to the illustrated embodiment in which the output signal of the eye-position detecting system 50 is inputted to the driver to energize the motor for adjusting the position of the ophthalmologic instrument, the present invention is not limited to such construction. It is to be understood that many changes and modifications may be made by those skilled in the art without departing the spirit and scope of the invention as defined in the appended claims.

For example, the present invention may provide such an arrangement that an ophthalmologic instrument is manually moved and adjusted in position by an operator, observing the amount and direction of a deviation which are displayed in any suitable displaying means.

Although the light emitting element 102 has described to be of DC type in the illustrated embodiment, a light emitting element of AC type may be used to improve S/M by adding some circuits.

If the amount and direction of a deviation only in Z-direction may be detected, a one-dimensional element may be used to locate along the scan direction of the chopper in place of the two-dimensional element in the illustrated and described embodiment.

Although the chopper 110 has described to locate in the light receiving side of the eye-position detecting system in the illustrated and described embodiment, the same chopper may be disposed between the light emitting element 102 and the projector lens 104.

The invention has thus been shown and described with reference to a specific embodiment, however, it should be noted that the invention is in no way limited to the details of the illustrated arrangements but changes and modifications may be made without departing from the scope of the appended claims.

We claim:

1. An apparatus for detecting a position of a patient's eye with respect to an ophthalmologic instrument, comprising a source of light for projecting a beam of light along an optical axis toward said eye, lens means for imaging the light beam reflected at a front portion of said eye, means for causing the light beam from said imaging means to scan at least in one direction, and means for detecting position of said light source by sensing the position of said light beam transmitted through said scanning means and providing a signal which can be used to detect the position of said eye with respect to said ophthalmologic instrument along the optical axis.

2. An apparatus as defined by claim 1 wherein said light source detecting means includes a photoelectric system for detecting the position of said light source along a linear line extending between said light source and said light source detecting means.

3. An apparatus as defined by claim 1 in which said scanning means includes chopper means for selectively passing the light beam to said detecting means.

4. An apparatus as defined by claim 1 in which said detecting means includes operating circuit means for calculating the position of said eye with respect to said instrument.

5. An apparatus as defined by claim 3 in which said scanning means includes a rotatable disc having a plurality of circumferentially spaced apertures for selectively passing the light beam.

* * * * *